United States Patent
Cattarini Mastelli et al.

(10) Patent No.: US 9,220,734 B2
(45) Date of Patent: Dec. 29, 2015

(54) INJECTABLE POLYDEOXYRIBONUCLEOTIDE COMPOSITION FOR THE TREATMENT OF OSTEOARTICULAR DISEASES

(75) Inventors: Laura Cattarini Mastelli, Taggia (IT); Giulia Cattarini Mastelli, Genoa (IT)

(73) Assignee: MASTELLI S.R.L., Sanremo (IM) (IT)

( * ) Notice: Subject to any disclaimer, the term of this patent is extended or adjusted under 35 U.S.C. 154(b) by 65 days.

(21) Appl. No.: 13/125,572

(22) PCT Filed: Oct. 28, 2009

(86) PCT No.: PCT/IB2009/054776
§ 371 (c)(1),
(2), (4) Date: Apr. 21, 2011

(87) PCT Pub. No.: WO2010/049898
PCT Pub. Date: May 6, 2010

(65) Prior Publication Data
US 2011/0196024 A1    Aug. 11, 2011

(30) Foreign Application Priority Data
Oct. 30, 2008    (IT) .............................. TO2008A0804

(51) Int. Cl.
*A61K 48/00* (2006.01)
*A61K 35/60* (2006.01)
*A61K 31/711* (2006.01)
*A61K 31/713* (2006.01)

(52) U.S. Cl.
CPC ............... *A61K 35/60* (2013.01); *A61K 31/711* (2013.01); *A61K 31/713* (2013.01)

(58) Field of Classification Search
CPC .................................................... A61K 31/711
See application file for complete search history.

(56) References Cited

U.S. PATENT DOCUMENTS 3,899,481 A * 8/1975 Butti et al. .................... 536/25.4
5,977,083 A * 11/1999 Burcoglu .................... 514/44 R

FOREIGN PATENT DOCUMENTS

| EP | 0226254 | 12/1993 |
| FR | 2676926 | 5/1991 |
| WO | 01/73003 | 10/2001 |
| WO | 03/035048 | 5/2003 |

OTHER PUBLICATIONS

Guizzardi, 2003, Life Sciences, 73:1973-1983.*
Vanelli, Knee Surg Sports Traumatol Arthrosc, 2010,18:901-907.*
Tonello, 1996, Jour Pharma Biomed Anal, 14:1555-1560.*
Chopra, 2000, Brit Jour Haematology, 111:1122-1129.*
Pescador, Seminars in Thrombosis and Hemostasis, 1996, 22:71-75.*
Saggini, Journal of Biological Regulators and Homeostatic Agents, 27:543-549, 2013.*
International Search Report for PCT/IB2009/054776 filed on Oct. 28, 2009 in the name of Medevice S.P.A.
Written Opinion for PCT/IB2009/054776 filed on Oct. 28, 2009 in the name of Medevice S.P.A.
Altman, R., et al., Development of criteria for the classification and reporting of osteoarthritis, Arthritis and Rheumatism 1986, 29: 1039-1049.
Karlsson, J., et al., Comparison of two hyaluronan drugs and placebo in patients with knee osteoarthritis. A controlled, randomized, double-blind, parallel-design multicentre study, Rheumatology 2002, 41: 4120-1248.

* cited by examiner

Primary Examiner — Valarie Bertoglio
(74) Attorney, Agent, or Firm — Steinfl & Bruno LLP

(57) ABSTRACT

Composition based on polynucleotides extracted from natural sources for use in therapeutic treatment and/or as a therapeutic co-adjuvant in the treatment of degenerative diseases of the joints, in particular osteoarthritis.

8 Claims, 4 Drawing Sheets

Figure 7:
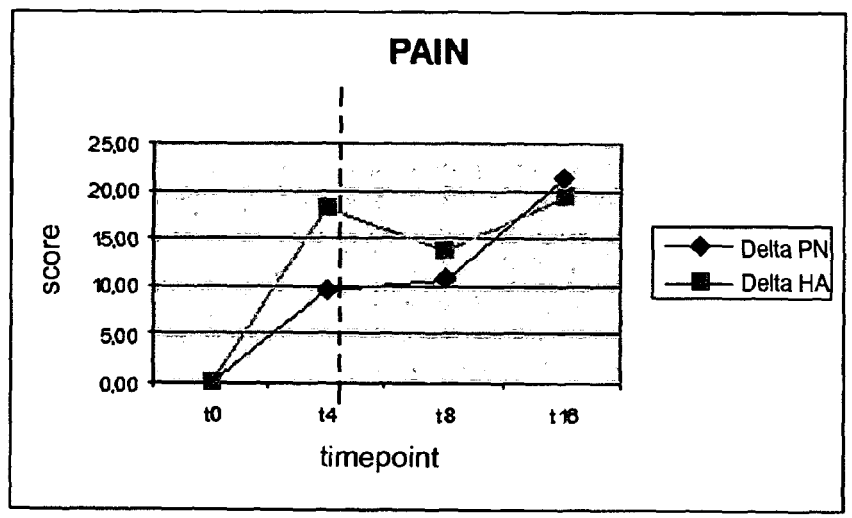

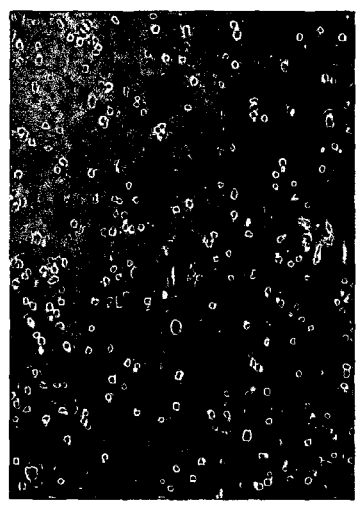
FIG.1 (CT)
FIG.2 (HA)
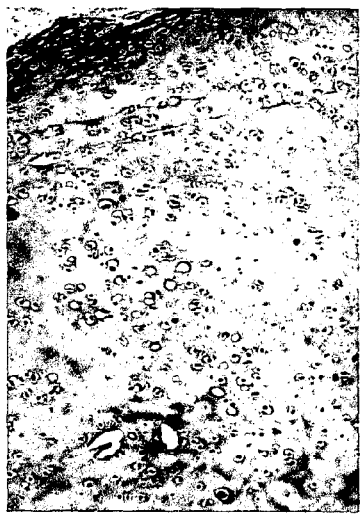
FIG.3 (PN)
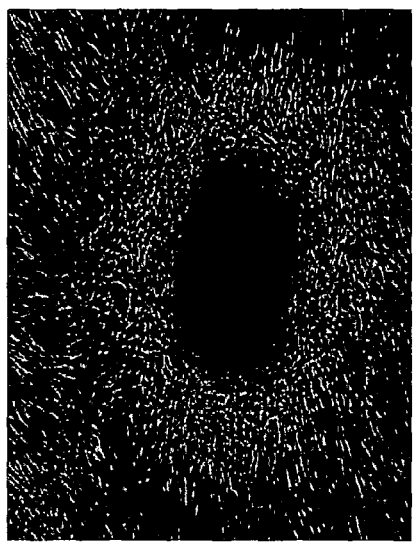
FIG.4
FIG.5
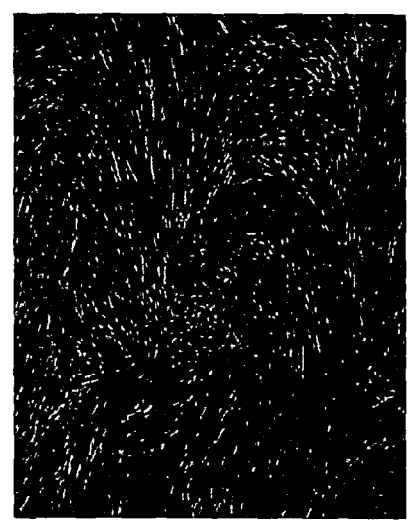
FIG.6

INJECTABLE POLYDEOXYRIBONUCLEOTIDE COMPOSITION FOR THE TREATMENT OF OSTEOARTICULAR DISEASES

CROSS REFERENCE TO RELATED APPLICATIONS

The present application is the US national stage of International Application PCT/IB2009/054776 filed on Oct. 28, 2009 which, in turn, claims priority to Italian Patent Application TO2008A000804 filed on Oct. 30, 2008.

This invention relates to a new use of a composition containing polydeoxyribonucleotides (hereinafter PDRN).

The composition used according to the invention comprises a fraction of PDRN polymer chains of different molecular weight, obtained from natural sources, of animal or plant origin, such as the placenta and the sperm of fish or plants.

Compositions based on PDRN as defined above are known and commercially available.

FR 2 676 926 describes pharmaceutical compositions containing highly polymerized polydeoxyribonucleotides obtained from fish sperm and used for the treatment or prevention of immunity deficits; compositions containing polydeoxyribonucleotides in a non-ionic solvent which can be used parenterally, particularly intramuscularly and/or intravenously, are described.

Processes for the preparation of polydeoxyribonucleotides obtained from mammal placentas are described in EP 0 226 254.

This invention relates to PDRN compositions extracted from natural sources for use in therapeutic treatment and/or as a therapeutic co-adjuvant in the treatment of osteoarticular diseases, in particular osteoarthritis, administered within the joint.

Another object of the invention is the use of a PDRN composition for the production of a medical device useful in the co-adjuvant treatment of degenerative diseases of the joints.

In the context of the invention intra-articular injectable formulations containing a highly-purified PDRN fraction, preferably of purity over 95% and more preferably over 98%, preferably obtained from fish sperm, are used.

The PDRN used preferably have a molecular weight of between 20 kDalton and 2500 kDalton, more preferably between 70 kDalton and 240 kDalton.

Typically, in the formulations used the PDRN fraction is present in a concentration from 0.1% to 10% by weight, preferably from 0.5 to 3% by weight in aqueous saline solvent, the said weight relating to the total weight of the formulation.

The aqueous saline solvent preferably contains sodium chloride and a mixture of sodium dihydrogen phosphate and sodium hydrogen phosphate.

The PDRN used may be obtained from an animal or plant source which is rich in DNA using the processes described in the abovementioned literature; the choice of fish sperm being preferred. By way of example, a PDRN which can be used in the context of the invention may be obtained by a process comprising the stages of:
1) enzyme lysis of the protein organic matrix
2) clarifying filtration of the resulting solution
3) precipitation with quaternary ammonium salts
4) decomplexing of the precipitate
5) molecular selection using column chromatography
6) precipitation of the eluate using alcohol.

In particular, an injectable product, drug or medical device according to the invention is provided in the form of a vial or bottle or in the form of a pre-filled syringe containing a metered quantity of PDRN, for example from 1 ml to 4 ml (preferably 2 ml) of PDRN solution in a concentration from 1 mg/ml to 100 mg/ml (preferably 5-30, and in particular approximately 20 mg/ml), with a pH from 6.5 to 7.5 and having a viscous consistency with a humectant, lubricant and trophic function.

A composition according to the invention, hereinafter referred to as CONDROTIDE, has the following characteristics:
appearance: clear solution
colour: colourless
pH: 6.5-7.5
volume which can be extracted from the syringe: 2.00-2.05 ml
osmolarity: 270-330 mOs/kg
UV identification of PDRN: maximum absorption 258±2 nm
UV metering of PDRN: 18-22 mg/ml
sterility: sterile (sterilisation performed at T>100, typically 120-121° C. for times of preferably 15 minutes)
bacterial endotoxin: ≤70 EU/ml.

The new use of the PDRN composition to which the invention relates is based on the following experimental observations.

Experimental pharmacology investigations in vitro performed when developing the invention have shown that the PDRN molecules present in the compositions according to the invention have an important trophic action on primary cultures of synovial cells, chondrocytes and cartilaginous biopsies, this observation being consistent with the clinical observation that the results of activity of the said compositions (CONDROTIDE) can improve and be maintained over time, unlike the results produced by hyaluronic acid.

In particular it has been shown (through cytofluorimetric analyses and specific staining) that the production of extracellular matrix (type II collagen and aggrecan) is strongly induced in cell cultures kept in a medium supplemented with 0.01% of CONDROTIDE for two weeks; control cultures kept in a medium supplemented with 1% of hyaluronic acid showed significantly less production of cell matrix.

Histological analyses of cartilaginous biopsies kept in culture for three weeks using a standard medium with added hyaluronic acid (1%) or CONDROTIDE (0.01%) have also been carried out. Histological examination again showed greater production of extracellular matrix in samples treated with CONDROTIDE in comparison to those to which hyaluronic acid had been added.

In particular, what is reported above is the result of the following experiments.

EXPERIMENT 1

Cartilaginous Biopsies

The investigation was carried out in order to evaluate the effects of CONDROTIDE (formulation indicated above) and hyaluronic acid on fragments of ex-vivo cartilaginous tissue (for three weeks), comparing them with those of a standard solution normally used in the laboratory for the maintenance of cartilaginous biopsies.

Sample: cartilaginous biopsies obtained from surgery.
Experimental Groups:
1. PN: biopsies held in "cartilaginous" medium+0.01% CONDROTIDE, 2. HA: biopsies held in "cartilaginous" medium+1% hyaluronic acid, 3. CT: biopsies held in "cartilaginous" medium without supplements.

End point: Histological analysis.

Results

The results of histological analysis of the biopsies are illustrated in FIGS. 1 to 3, which relate to haematoxylin-eosin sections obtained from cartilaginous biopsies fixed in formalin and impregnated in paraffin, where:

FIG. 1: a biopsy for the control group (CT): a decalcified fragment of joint cartilage, a normal slightly-eosinophilic cartilaginous matrix and a cell cluster immersed in the cartilage matrix will be seen, FIG. 2: biopsy for the HA group: a decalcified fragment of cartilage, the presence of tissue similar to bone and the absence of normal cartilaginous matrix will be seen, FIG. 3: biopsies after three weeks for the PN group: a decalcified fragment of cartilage, a slightly-eosinophilic cartilaginous matrix and a normal cartilaginous matrix surrounding the chondrocytes will be seen.

Histological analysis for the PN group also indicates a situation which is almost identical to that for the positive control CT, that is the phenotypic characteristics specific to hyalin joint cartilage are maintained. Conversely, the group treated with HA developed abnormal characteristics, such as the formation of immature bone elements and absence of a normal extracellular matrix.

EXPERIMENT 2

Isolated Cartilaginous Cells (Chondrocytes)

The investigation was carried out in order to evaluate the effects of the formulation according to the invention (CONDROTIDE) and hyaluronic acid on isolated chondrocyte cells (two weeks' culture), comparing them with those for a standard medium normally used in the laboratory for the culture of chondrocytes.

Sample: Isolated human chondrocytes.

Experimental Groups:

4. PN: cells held in "cartilaginous" medium+0.01% CONDROTIDE,

5. HA: cells held in "cartilaginous" medium+1% hyaluronic acid,

6. CT: cells held in "cartilaginous" medium without supplement.

End point: Immunohistochemistry, FACS analysis, Alcian Blue Staining.

Results

FIGS. 4 and 6 illustrate the results of staining with Alcian Blue (which is capable of revealing the presence of extracellular matrix):

FIG. 4: control group: highly expressed matrix,

FIG. 5: HA group: weakly expressed matrix,

FIG. 6: PN group: highly expressed matrix.

It is concluded that CONDROTIDE 0.01% is capable of inducing the production of extracellular matrix in quantities which are very much greater than hyaluronic acid in isolated chondrocyte cultures.

These data have been confirmed by a FACS analysis and an immunohistochemical analysis which has demonstrated that the profile of the expression and production of aggrecan and type II collagen is significantly less in the HA group in comparison with the PN and CT groups.

Results of the preliminary in vitro investigation support the observation that hyaluronic acid is only useful for improving symptoms for a short period of time, whereas the formulation according to the invention (CONDROTIDE) has proved to be very much more active in the treatment of joint diseases, with lasting results.

In support of the in vitro tests mentioned above an experiment was performed to check the effects of the formulation according to the invention administered intra-articularly to patients suffering from osteoarthritis of the knee, with the specific objective of evaluating efficacy, safety and tolerance for that formulation (CONDROTIDE, class III medical device).

The investigation was carried out in accordance with the guidelines of the Helsinki Declaration of 1974 and subsequent updates and the general principles of "ICH Harmonized Tripartite Guidelines for Good Clinical Practice (GCP)". Before starting the investigation approval was obtained from the Bioethics Committee of the Fondazione IRCCS Policlinico San Matteo of the University of Pavia. All the patients were informed about the clinical trial and the investigator obtained written informed consent from all patients before enrolment.

The design of the investigation and the controlled clinical trial against hyaluronic acid was double-blind randomised in parallel groups.

Each patient was randomly assigned to one of the following treatment groups:

group A: PDRN (abovementioned CONDROTIDE formulation), group B: hyaluronic acid (SINOVIAL).

Every patient was followed up for a period of sixteen weeks. Because the two different preparations could be identified by the operator in the instillation process, the blind-observer technique was used to maintain double-blind conditions. The investigator administering the product was different from the investigator who examined the patient clinically and evaluated the efficacy and safety of the product. In this way neither the patient nor the investigator were aware of the nature of the treatment.

Sample Size

Calculation of the sample size was based on an unpaired t-test with a probability level of 5%, a standard deviation of 3 cm and a desired power of 80% to detect a 1.6 cm difference in the reduction of pain measured through VAS (Rheumatology 2002; 41:1240-1248). A total sample size of 56 patients was calculated, and therefore provision was made for enrolling at least 60 patients, 30 per group.

Patients

Patients suffering from osteoarthritis of the knee (according to ACR classification—Arthritis Rheum. 1986; 29(8): 1039-49) were recruited. In particular the product used in the investigation had the following composition:

polydeoxyribonucleotides: 20 mg sodium chloride: 4 mg sodium dihydrogen phosphate dihydrate: 0.2 mg sodium hydrogen phosphate dodecahydrate: 1 mg water for injectable preparations: q.s. 1 ml.

A solution of hyaluronic acid under the trade name of SINOVIAL, containing the highly-purified sodium salt of hyaluronic acid having a molecular weight between 800 kDalton and 1200 kDalton, was used as the control product.

Composition: Sodium salt of hyaluronic acid: 0.8%, sodium chloride, sodium phosphate and water for USP injectable preparations (q.s.).

Pharmaceutical form: Syringes prefilled with 16.0 mg of hyaluronic acid in 2 ml of buffered sodium chloride saline solution.

Dosage and Method Administration of the Treatment

Intra-articular treatment with PDRN gel comprised five instillations of 2 ml on a weekly basis.

The control group with hyaluronic acid was treated with intra-articular instillations of sodium hyaluronate (16.0 mg of hyaluronic acid in 2 ml). This solution was also applied as five instillations on a weekly basis.

The product (CONDROTIDE or SINOVIAL) was injected into the joint cavity of the affected knee using a sterile needle.

Duration of the Treatment

The treatment was administered with one instillation into the affected knee per week for a total of five instillations; the treatment time was therefore four weeks, but each patient was followed up for a total of sixteen weeks.

Clinical Evaluations

Clinical evaluations were made of each patient at the start of the investigation (T0), and one (T1), two (T2), three (T3) and four (T4) weeks after the start of the investigation. T4 corresponds to the end of the treatment stage. Follow-up clinical evaluations were made one month after the end of the treatment (T8) and three months after the end of treatment (T16).

The main evaluation parameter (primary end point) was the pain level evaluated at rest, during loading and physical activity. A visual-analogue scale (VAS in cm from 0 to 10) was used to evaluate pain. Crepitation on movement, restriction of joint motility and joint oedema were also evaluated, recorded on a score from 0 to 3 (0=absent, 1=mild, 2=moderate, 3=severe) on every examination.

A self-assessment questionnaire was also compiled by the patients—the Knee and Osteoarthritis Outcome Score—KOOS. The KOOS is a scale for evaluating degree of osteoarthritis developed as an extension of the WOMAC (Western Ontario and MacMaster University) Osteoarthritis Index to generate a useful and universally-accepted tool to determine the effectiveness of treatments in clinical trials.

Figure 8:
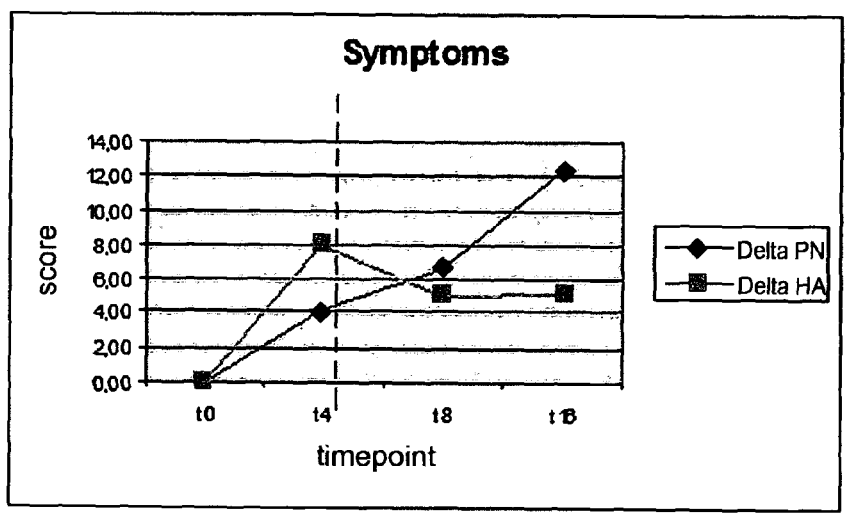
Figure 9:
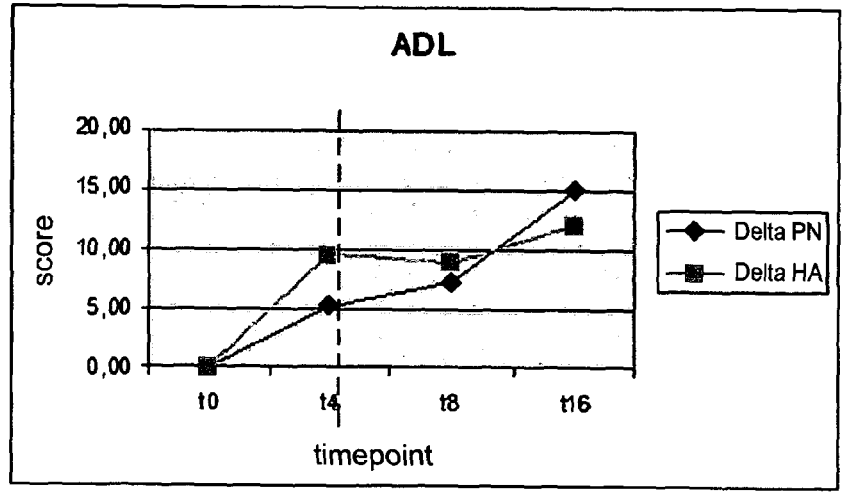
Figure 10:
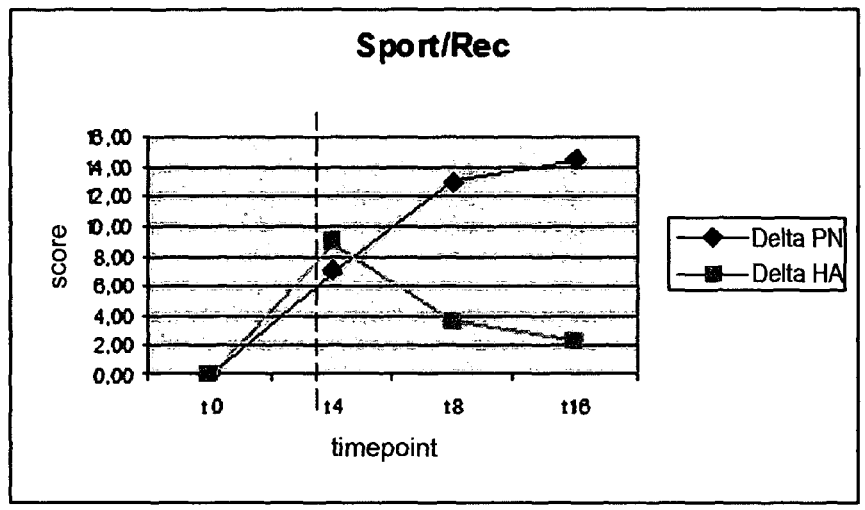
Figure 11:
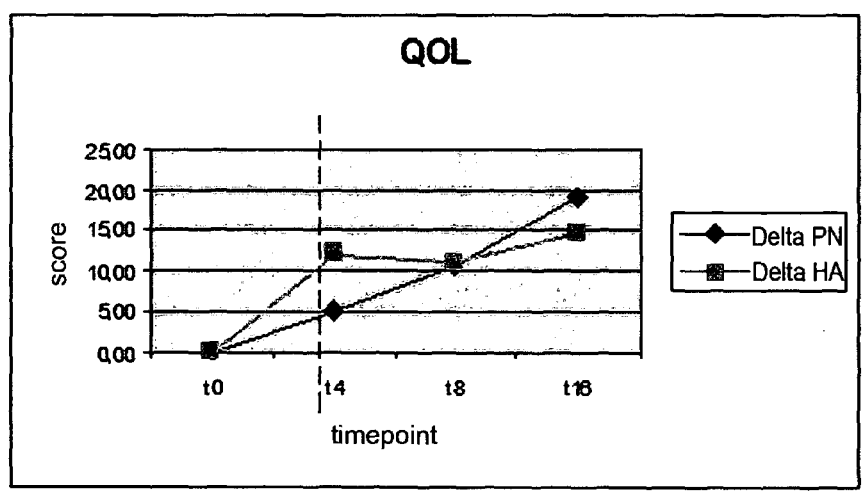

This questionnaire is a specific tool for evaluating patients' opinions concerning their knees. The questionnaire comprises five subscales (pain, FIG. 7), other symptoms (FIG. 8), joint function in daily life (ADL, FIG. 9), joint function in sports/recreational activities (sport/rec, FIG. 10) and quality of life (QOL, FIG. 11).

The KOOS were compiled by patients at the time of the following examinations, T0, T4, T8 and T16, considering the week preceding the examination in their responses to the questions. Five response options were provided in the KOOS questionnaire, each response obtaining a score of between 0 and 4.

On the basis of statistical analysis of the data polynucleotides proved to have a statistically significant greater effect on resting pain, pain on loading, crepitation and reducing oedema and restricted joint motility than the control with hyaluronic acid.

These data show the statistically-significant better effect of PDRN in comparison with hyaluronic acid.

As far as the data relating to resting pain are concerned, by analysing the differences between the basic values and their change in the course of treatment (Delta), the data illustrated below were obtained and indicate an obvious overall trend on the part of PDRN to achieve final values which are better than those obtained in patients treated with hyaluronic acid.

Figure 12:
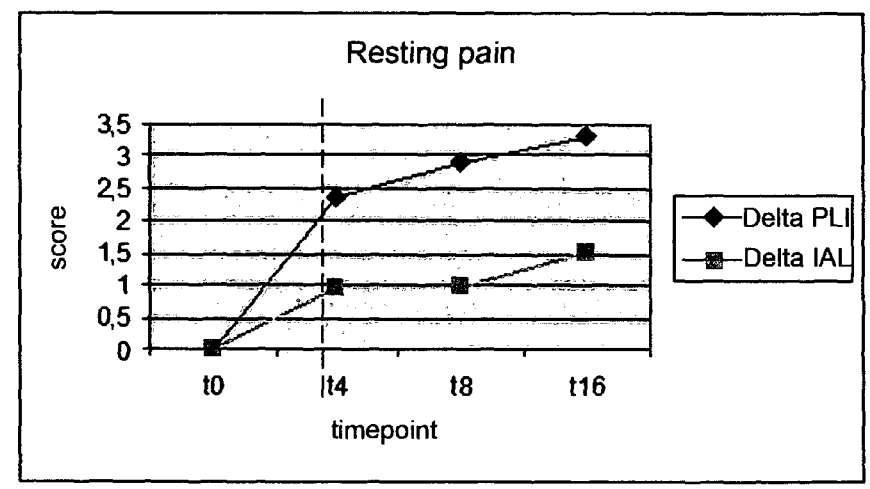

The results are illustrated in FIG. 12, where the dotted vertical line in the graph divides each diagram into two parts, corresponding to the treatment period (left-hand half) and the follow-up period (right-hand half).

Figure 13:
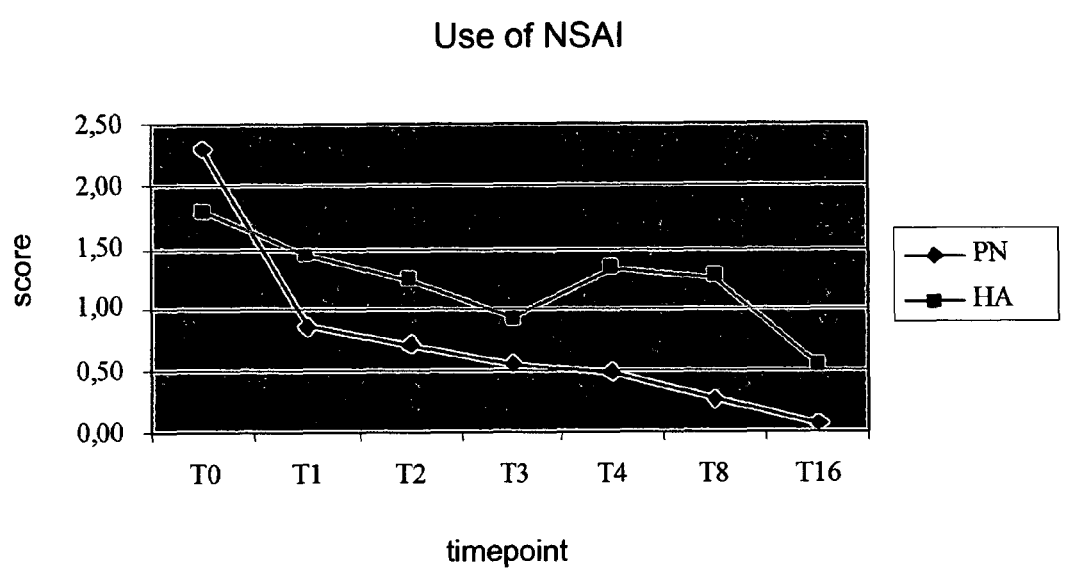

In the course of the investigation the patients were allowed to use non-steroid anti-inflammatories (NSAI) if necessary in order to reduce painful symptoms. The recorded data relating to the use of NSAI (see the diagram in FIG. 13) show an obvious greater consumption at the start of the trial (T0) in the group of treated patients in comparison with controls, yielding a statistically significant difference in that there was a reduction in the use of these drugs in the treated group which was not seen in the control group.

In addition to this, as treatment progressed there was a marked and rapid reduction in the consumption of NSAI in the group treated with PDRN after just one intra-articular instillation (T1). In addition to this there was a continuing lesser use of NSAI in the PDRN group at all subsequent times, with a particular difference between the two treatments at T4 and T8.

As will be seen from the data in FIGS. 7 to 11, during the treatment period the products tested brought about an improvement in all the KOOS indicators; this improvement was slightly faster in the control group. However, if the shape of the graphs in the follow-up period is observed it will be seen that the score for the hyaluronic acid group decreases or remains constant, while the score for the PDRN group continues to increase.

Three months after the end of treatment (T16) the scores for the PDRN group were in all cases higher than those for the hyaluronic acid group; the difference is particularly obvious for the symptoms and sport/rec subscales.

In the latter scale, which represents the function of the joint during and after motor activity, the control group (hyaluronic acid) reverted to almost the initial values, while the group treated with PDRN showed an overall improvement of 14.55 points (it will not be forgotten that an improvement in the KOOS scale is clinically significant if the score increases by 8-10 points in the course of treatment).

The data obtained support use of the formulation according to the invention in therapeutic treatment and as a therapeutic co-adjuvant in the treatment of degenerative diseases of the joints, such as in particular osteoarthritis.

At the present time there is no definitively effective treatment for these diseases; proposed treatments include anti-inflammatories, pain relievers, steroids, physiotherapy and surgery, as well as supplementing the viscosity of the synovial fluid through the intra-articular instillation of hyaluronic acid, used in the control tests described above.

It should be borne in mind that the better effect revealed by the PDRN formulation included in the formulation according to the invention is due to the fact that PDRN are capable of binding an appreciable quantity of water and reorganising their own structure, orientating and coordinating the water modules, so as to form a proper gel.

The device according to the invention, injected intra-articularly, provides a viscoelastic supplement for the synovial fluid and can thoroughly lubricate joint surfaces. In addition to this, it can be presumed that the polydeoxyribonucleotide micromolecules are at the same time subject to the action of lytic enzymes which progressively release PDRN of progressively smaller size into the joint cavity.

Intra-articular instillation using the formulation according to the invention progressively enriches the synovial fluid, initially with polynucleotide macromolecules having a viscoelastic action and over time with polynucleotides and nucleotides which are used by the tissues to improve cellular activity and to protect and promote the physiological mechanisms of joint cartilage regeneration.

Thus the viscoelastic and lubricating action of the product is combined with a biostimulant and trophic effect on joint cartilage.

It is concluded from this that the formulation according to the invention is of general use for the treatment of painful joint diseases which can be ascribed to degenerative or post-traumatic conditions or changes in joints.

The invention claimed is:

1. A method of treating osteoarthritis in a subject, the method comprising administering intra-articularly to the subject an effective amount to treat the osteoarthritis, of a composition comprising polydeoxyribonucleotides, extracted from fish sperm, wherein the polydeoxyribonucleotides have molecular weights of from 70 kDalton to 240 kDalton wherein the composition is administered as a viscolastic supplement for the synovial fluid of the joint, wherein said administering results in improved Knee injury and Osteoarthritis Outcome Score (KOOS) indicator scores.

2. The method according to claim 1, wherein the composition is in form of an injectable aqueous solution containing from 1 to 100 mg/ of polydeoxyribonucleotide in a saline aqueous solvent.

3. The method according to claim 2, wherein the injectable aqueous solution has a pH of from 6.5 to 7.5.

4. The method according to claim 2, wherein the injectable aqueous solution contains sodium chloride and sodium phosphate salts.

5. The method according to claim 1, wherein the effective amount is administered to induce production of extracellular matrix in the subject, the extracellular matrix including type II collagen and aggrecan.

6. A method of treating pain in a patient suffering from osteoarthritis, the method comprising administering intra-articularly to the patient an effective amount of a composition comprising polydeoxyribonucleotides, extracted from fish sperm, wherein the polydeoxyribonucleotides have molecular weights of from 70 kDalton to 240 kDalton, wherein said administering results in decreased pain.

7. The method according to claim 6, wherein the composition is administered as a co-adjuvant in a therapeutical treatment of the osteoarthritis.

8. The method according to claim 1, wherein the composition is in form of an injectable aqueous solution containing from 5 to 30 mg/ml of polydeoxyribonucleotide in a saline aqueous solvent.

* * * * *